US009974783B2

(12) United States Patent
Zagon et al.

(10) Patent No.: US 9,974,783 B2
(45) Date of Patent: *May 22, 2018

(54) METHODS AND COMPOSITIONS FOR TREATMENT OF EPITHELIAL WOUNDS (71) Applicant: THE PENN STATE RESEARCH FOUNDATION, University Park, PA (US)

(72) Inventors: Ian S. Zagon, Hummelstown, PA (US); Patricia J. McLaughlin, Harrisburg, PA (US); Joseph W. Sassani, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/067,604

(22) Filed: Mar. 11, 2016

(65) Prior Publication Data
US 2016/0250206 A1 Sep. 1, 2016

Related U.S. Application Data (62) Division of application No. 14/235,610, filed as application No. PCT/US2012/048236 on Jul. 26, 2012, now Pat. No. 9,283,175.

(60) Provisional application No. 61/512,577, filed on Jul. 28, 2011.

(51) Int. Cl.
A61K 31/44 (2006.01)
A61K 9/00 (2006.01)
A61K 31/485 (2006.01)
A61K 9/06 (2006.01)
A61K 9/08 (2006.01)
A61K 9/70 (2006.01)
A61K 45/06 (2006.01)

(52) U.S. Cl.
CPC .......... A61K 31/485 (2013.01); A61K 9/0014 (2013.01); A61K 9/06 (2013.01); A61K 9/08 (2013.01); A61K 9/70 (2013.01); A61K 45/06 (2013.01)

(58) Field of Classification Search
CPC ...... A61K 31/485; A61K 9/0014; A61K 9/06; A61K 9/08; A61K 9/70; A61K 45/06
USPC ........................................................ 514/282
See application file for complete search history.

(56) References Cited

U.S. PATENT DOCUMENTS 5,266,574 A 11/1993 Zagon et al.
5,834,480 A * 11/1998 Elkhoury ............. A61K 31/485
514/289
7,939,567 B2 5/2011 Wu et al.
9,283,175 B2 * 3/2016 Zagon .................. A61K 31/485
2007/0203164 A1 8/2007 Chiang et al.
2011/0082167 A1 4/2011 Pisak et al.

FOREIGN PATENT DOCUMENTS

CN 101272787 A 9/2008
WO 2004091593 A2 10/2004
WO 2007097765 A1 8/2007
WO 2009120889 A2 10/2009

OTHER PUBLICATIONS

Chinese Office Action dated Oct. 13, 2015 issued in corresponding Chinese Patent Application No. 201280045432.3. (English-language translation only).
Chinese Office Action dated Jan. 29, 2015 from related Chinese Application No. 201280045432.3, together with an English language translation.
Reece, A.S., et al., "Chronic Ulcers Caused by Injection of Substances: Healing Aided by Naltrexone", Archives of Dermatology, vol. 145, No. 4, pp. 375-377 (Apr. 2009).
McLaughlin, P.J., "Diabetic Keratopathy and treatment by modulation of the opioid growth factor (OGF)-OGF receptor (OGFr) axis with naltrexone: a review", Brain Research Bulletin, vol. 81, No. 2-3, pp. 236-247 (Feb. 15, 2010).
Klocek, M. S., "Topically Naltrexone Restores Corneal Reepithelialization in Diabetic Rats", Journal of Ocular Pharmacology and Therapeutics, vol. 23, No. 2, pp. 89-102 (Apr. 1, 2007).
Extended Supplementary European Search Report dated Mar. 27, 2015 from related European Application No. 12 81 7917.3.
Immonen JA et al.. "Topical Treatment With the Opioid Antagonist Naltrexone Accelerates the Remodeling Phase of Full-Thickness Wound Healing in Type 1 Diabetic Rats". Experimental Biology and Medicine 238:1127-1135 (Oct. 2013).
McLaughlin P.J. et al.. "Topical Naltrexone Accelerates Full-Thickness Wound Closure in Type 1 Diabetic Rats by Stimulating Angiogenesis", Experimental Biology and Medicine 0:1-11 (2013).
McLaughlin P.J. et al., "Topical Treatment With the Opioid Antagonist Naltrexone Facilitates Closure of Full-Thickness Wounds in Diabetic Rats", Experimental Biology and Medicine 236:1122-1132 (Oct. 2011).
Zagon I.S. et al., "Naltrexone, an Opioid Antagonist, Facilitates Reepithelialization ofthe Cornea in Diabetic Rat", Diabetes 51: 3055-2062 (Oct. 2002).
Zagon I.S. et al., "Naltrexone Accelerates Healing Without Compromise of Adhesion Complexes in Normal and Diabetic Corneal Epithelium", Brain Research Bulletin 72:18-24 (2007).
International Preliminary Report on Patentability dated Jan. 28, 2014 received from related International Application No. PCT/US2012/048236.

(Continued)

Primary Examiner — My-Chau T. Tran
(74) Attorney, Agent, or Firm — John P. Zimmer; Nexsen Pruet, PLLC (57) ABSTRACT The invention relates to treatment of epithelial wounds. In particular, the invention relates to methods and formulations for treating epithelial wounds based on application of an opioid antagonist such as naltrexone.

9 Claims, 10 Drawing Sheets (56) References Cited

OTHER PUBLICATIONS

Australian Government—IP Australia. Examination Report No. 2 for Standard Patent Application dated Jan. 6, 2017, Australian Application No. 2012286843. Name of Applicant: Patricia J. McLaughlin et al. English Language. 13 pages.

Pothering, C. "Topical Naltrexone Accelerates Full Thickness Wound Healing in Normal and Type 1 Diabetic Rats". Masters's Tesis, 2009. Department of Neural and Behavioral Sciences. The Pennsylvania State University. Retrieved from https://etda.libraries.psu.edu/catalog/9416. English Language. 3 pages. Retrieved Apr. 24, 2017.

* cited by examiner

METHODS AND COMPOSITIONS FOR TREATMENT OF EPITHELIAL WOUNDS

CROSS REFERENCE TO RELATED APPLICATIONS

This application is a divisional of U.S. application Ser. No. 14/235,610, filed Jan. 28, 2014, allowed, which is a U.S. national stage application under 35 U.S.C. § 371 of International Application No. PCT/US2012/048236, filed Jul. 26, 2012, which claims priority to U.S. provisional application 61/512,577, filed Jul. 28, 2011, each of which is incorporated herein by reference in its entirety.

FIELD OF THE INVENTION

This invention relates to treatment of epithelial wounds. In particular, the invention relates to methods and formulations for treating epithelial wounds based on application of opioid antagonists such as naltrexone.

BACKGROUND OF THE INVENTION

Wound healing is a carefully orchestrated series of events with overlapping temporal and spatial relationships, and includes phases of inflammation, proliferation, and remodeling (Guo et al., *Journal Dent Res,* 89:219-229 (2010); Shih et al., *Wound Repair Regeneration,* 18:139-153 (2010)). Some of the processes in wound repair that have been implicated as responsible factors include abnormalities in inflammation, migration, angiogenesis, neovascularization, cell proliferation, formation of granulation tissue and collagen, and re-epithelialization (Usui et al., *Journal of Histochem Cytochem,* 56:687-696 (2008); Mustoe et al, *American Journal of Surgery,* 187:655-705 (2004); Brem et al., *Arch Surg,* 135:627-634 (2000)).

In Type 1 diabetes, wounds often fail to progress through the normal stages of healing (Boulton et al., *Lancet,* 366: 1719-1724 (2005); Usui et al., *Journal of Histochem Cytochem,* 56:687-696 (2008)). Impaired wound healing is a major complication of diabetes that can result in the formation of chronic debilitating ulcers (Guo et al., *Journal Dent Res,* 89:219-229 (2010); Boulton et al., *Lancet,* 366:1719-1724 (2005); O'Loughlin et al., *International Journal of Lower Extremity Wounds,* 9:90-102 (2010)). Diabetes is the leading cause of amputations (Boulton et al., *Lancet,* 366: 1719-1724 (2005); O'Loughlin et al., *International Journal of Lower Extremity Wounds,* 9:90-102 (2010)), accounting for over 50% of patients having lower extremity amputations annually. With the number of diabetic patients estimated to reach 300 million world-wide by the year 2030, the burden of diabetic wounds and their complications is expected to rise simultaneously (Boulton et al., *Lancet,* 366:1719-1724 (2005)). Although continuing medical care and patient self-management reduce the risk of long-term complications, and despite the availability of numerous dressing products, there is no fully effective prevention or treatment of these complications.

Initially studied for their role as neurotransmitters (Akil et al., *Ann Rev Neuroscience,* 7:223-255 (1984)), endogenous opioids have been shown to be present in neural and non-neural tissues, and to mediate a number of functions other than neuromodulation including cell proliferation, angiogenesis, tissue organization, cell migration, and immunity (Zagon et al., *Journal of Invest Dermatology,* 106:490-497 (1996); Zagon et al., *Diabetes,* 51:3055-3062 (2002); Zagon et al., *Journal of Vascular Surgery,* 37:636-643 (2003); Blebea et al., *Journal of Vascular Surgery,* 32:364-373 (2000); Zagon et al., *Immunobiology,* 216:173-183 (2011); Zagon et al., *Immunobiology,* 216:579-590 (2011); Wilson et al., *Cell Prolif* 33:63-73 (2000)). The endogenous opioids include dynorphins, enkephalins, endorphins, endomorphins and nociceptin. Classical opioid receptors are the μ, δ, and κ receptors; non-classical opioid receptors include the nociceptin receptor and the opioid growth factor receptor (OGFr), also referred to as the ξ (zeta) receptor (Corbett et al. *Br. J. Pharmacol.* 147 Suppl 1: S153-62 (2006)). The endogenous ligand for OGFr is [Met$^5$]-enkephalin, also called opioid growth factor (OGF).

The relationship of native opioids to diabetes has received some attention. Studies concerned with circulating opioid levels in diabetes have shown that patients with type 1 diabetes (T1D) have high plasma [Met$^5$]-enkephalin levels (Fallucca et al., *Metabolism,* 45:1065-1068 (1996); Negri et al., *Metabolism,* 41:460-461 (1992); Kolta et al., *Neuropeptides,* 21:55-63 (1992)). Elevated levels of [Met$^5$]-enkephalin also have been reported in plasma of genetically obese diabetic (db/db) mice (Timmers et al., *Diabetes,* 35:1143-1151 (1986); Greenberg et al. *Endocrinology,* 116:328-331 (1985)).

A series of studies using systemic and topical applications of the opioid antagonist naltrexone (NTX) in rats with T1D reported delays in re-epithelialization following removal of ocular surface epithelium that were reversed by NTX and related to an increase in DNA synthesis (Zagon et al., *Diabetes,* 51:3055-3062 (2002); Klocek et al., *Journal of Ocular Pharmacology and Therapeutics,* 23:89-102 (2007)). These data suggest that dysfunctional ocular wound repair in T1D was due to an increase in opioid peptide-opioid receptor interactions that were disrupted by NTX. OGF is known to suppress re-epithelialization in the human cornea (Zagon et al., *Investigative Ophthalmology & Visual Science,* 41:73-81 (2000)) and rat tail skin (Wilson et al., *Cell Prolif* 33:63-73 (2000)).

Endogenous opioids, and classical and non-classical opioid receptors, are present in epithelial tissues (Cheng et al., *Clin Lab Invest,* 158:713-720 (2008); Wintzen et al., *Exp Dermatol,* 10:305-311 (2001); Tominaga *Journal of Invest Dermatol,* 127:2228-2235 (2007); Bigliardi-Qi et al., *Differentiation,* 74:174-185 (2006); Nissen et al., *Experimental Dermatology,* 6:222-229 (1997); Wenk et al., *Journal of Comp Neurol,* 408:567-579 (1999); Salemi et al., *Biochem Biophys Res Commun,* 338:1012-1017 (2005); Zagon et al., *Cell Tissue Research,* 246:561-565 (1986); Bigliardi et al., *Journal of Invest Dermatol,* 111:297-301 (1998); Kauser et al., *Journal of Invest Dermatol,* 120:1073-1080 (2003)). OGF is known to regulate DNA synthesis and cellular renewal of the stratum corneum, (Wintzen et al., *Exp Dermatol,* 10:305-311 (2001)) whereas deletion of the δ opioid receptor in mice alters skin differentiation and delays wound healing (Bigliardi-Qi et al., *Differentiation,* 74:174-185 (2006)).

There is an urgent need to understand the pathophysiology underlying wound healing in diabetes and other situations in which wound healing is delayed, and to translate this knowledge into treatment modalities in order to prevent or at least attenuate acute and chronic wound healing complications (Usui et al., *Journal of Histochem Cytochem,* 56:687-696 (2008)).

SUMMARY OF THE INVENTION

In one embodiment, the present invention is directed to a method of treating epithelial wounds by administering an effective amount of an opioid antagonist to a subject in need thereof. In a specific embodiment, the opioid antagonist being administered is naltrexone. In another specific embodiment, the opioid antagonist being administered is naloxone.

In another embodiment, the present invention provides a composition for the treatment of epithelial wounds, which contains an effective amount of an opioid antagonist and a pharmaceutically acceptable carrier suitable for topical administration. In a specific embodiment, the opioid antagonist provided in the composition is naltrexone. In another specific embodiment, the opioid antagonist being administered is naloxone.

BRIEF DESCRIPTION OF THE DRAWINGS

FIG. 5. Histograms of residual defects (%) in rat skin after formation of 6 mm wounds and followed for 9 days. A. Normal and Diabetic (DB) rats receiving no treatment. B. Normal and Diabetic rats treated one time (1×) or 3 times (3×) daily with $10^{-5}$ M NTX dissolved in Neutrogena moisturizing cream (MCN+NTX 1×; MCN+NTX 3×) or receiving vehicle alone (MCN+Vehicle 1×; MCN+Vehicle 3×). C. The contribution of contraction and re-epithelialization to wound closure at 8 days in DB and Normal (N) rats treated with MCN+NTX or MCN+Vehicle. Values represent means±SEM. Significantly different from Normal or MCN+Vehicle at *$P<0.05$, $P<0.01$, and *$P<0.001$; ++$P<0.01$.

FIG. 6. Histograms of residual defects (%) in rat skin after formation of 6 mm wounds and followed for 9 days. Groups included Normal and Diabetic rats treated 3 times (3×) daily with $10^{-5}$ M NTX dissolved in Oil of Olay moisturizing cream (MCOO+NTX 3×) or receiving vehicle alone (MCOO+Vehicle 3×), or $10^{-5}$ M NTX dissolved in KY jelly (KYJ+NTX 3×) or KY jelly alone (KYJ+Vehicle 3×). Values represent means±SEM. Significantly different from the respective vehicle at *$P<0.05$, **$P<0.01$, <0.001.

DETAILED DESCRIPTION OF THE INVENTION

It has been surprisingly discovered by the inventors that topical administration of general or broad-based opioid antagonists can enhance and accelerate epithelial wound healing in both normal and diabetic subjects, and can restore the delayed rate of wound healing in diabetes to the rate in normal subjects. Accordingly, the present invention provides therapeutic methods and topical formulations for treating epithelial wounds in a subject, including especially a diabetic subject, based on use of naltrexone and other general opioid antagonists.

General opioid antagonists, such as naltrexone (also abbreviated herein as "NTX") and naloxone, are known as broad-based antagonists of opioid receptors and are used primarily in the management of dependence on drugs (e.g., opioids), alcohol, and nicotine. The beneficial effects of opioid antagonists on the wound healing process identified herein are surprising, especially in light of the reports that naltrexone is a poor penetrator of the skin (see, e.g., Stinchcomb et al., *J. Pharmaceutical Sciences* 91: 2571-2578, 2002); Krishman et al., *J. Pharmaceutical Sciences* 99: 2724-2731, 2010).

As disclosed herein, a marked increase in DNA synthesis of the stratum basale in skin was observed in diabetic animals exposed to NTX. At least one endogenous opioid system, the opioid growth factor-opioid growth factor receptor (OGF-OGFr) system, is known to tonically regulate cell proliferation through an increase in the cyclin dependent inhibitory kinase pathway (Cheng et al., *Molecular Biology of the Cell*, 20:319-327 (2009)). The OGF-OGFr axis has been reported to depress T- and B-cell proliferation (Zagon et al., *Immunobiology*, 216:173-183 (2011); Zagon et al., *Immunobiology*, 216:579-590 (2011)), cell migration (Zagon et al., *American Journal of Physiology*, 268:R942-R950 (1995)), proliferation of keratinocytes and fibroblasts (Zagon et al., *Journal of Invest Dermatology*, 106:490-497 (1996); Zagon et al. *Diabetes*, 51:3055-3062 (2002); Zagon et al., *Journal of Vascular Surgery*, 37:636-643 (2003); Blebea et al., *Journal of Vascular Surgery*, 32:364-373 (2000); Zagon et al., *Immunobiology*, 216:173-183 (2011); Zagon et al., *Immunobiology*, 216:579-590 (2011); Wilson et al., *Cell Prolif* 33:63-73 (2000); Zagon et al., *Investigative Ophthalmology & Visual Science*, 41:73-81 (2000)) and angiogenesis (ZAGON et al., *Journal of Vascular Surgery*, 37:636-643 (2003); Blebea et al., *Journal of Vascular Surgery*, 32:364-373 (2000)), all of which have been implicated as factors in diabetic complications.

Interestingly, patients with T1D as well as mice with Type 2 diabetes (T2D) have elevated levels of OGF ([Met$^5$]-enkephalin) (Fallucca et al., *Metabolism*, 45:1065-1068 (1996); Negri et al., *Metabolism*, 41:460-461 (1992); Kolta et al., *Neuropeptides*, 21:55-63 (1992); Timmers et al., *Diabetes*, 35:1143-1151 (1986); Greenberg et al. *Endocrinology*, 116:328-331 (1985)), suggesting that diabetes is accompanied by an increase in an opioid peptide associated with an inhibition of cell replication. Hence, without being bound to any particular theory, it is postulated that excessive OGF-OGFr interaction retards wound closure such as is found in diabetes. Moreover, interruption of this activity by NTX is responsible, at least in part, for restoring related processes to a normal condition.

Conditions associated with delayed wound healing include diabetes (both Type 1/insulin-dependent diabetes, and Type 2/non-insulin dependent diabetes), obesity, increasing age of the subject, coronary artery disease, peripheral vascular disease, wound infection, cancer, and immunosuppression including immune system compromise and immunosuppressive or radiation therapies. The use of administration of opioid antagonists such as NTX and naloxone to promote wound healing where any of these conditions is present in a subject is encompassed by the disclosure herein. The inventors have discovered that administration of opioid antagonists promotes wound healing even in normal subjects; thus the methods and compositions of the invention can be beneficial in any situation where improved epithelial wound treatment is desired. Without being bound, it is believed that the opioid antagonists promote wound healing in part through interaction with the opioid growth factor receptor (OGFr). Accordingly, in one embodiment, the methods and compositions provided herein are administered to an epithelial wound where OGFr is present or expressed on epithelial cells adjacent to or forming the epithelial wound.

The studies presented herein identify improved wound healing in both T1D and T2D model animals; thus the methods and compositions provided herein are applicable to treatment of epithelial wounds in a subject with any form of diabetes.

Subjects which can be treated using the disclosed methods include any mammalian subjects, particularly human subjects, dogs, cats and horses, which can be a diabetic or non-diabetic subject.

Epithelial wounds which can be effectively treated in accordance with this disclosure include epidermal wounds involving cells and tissue in the epidermis (such as any of the five epidermal layers: stratum basale, stratum spinosum, stratum granulosum, stratum licidum, and stratum corneum); dermal wounds involving cells and tissue in the dermis of the skin; and wounds involving interior epithelial surfaces of the body, such as the epithelial lining of internal organs and body cavities. Thus, the methods and compositions of the invention can be used to treat surface wounds such as skin abrasions, wounds involving injury to the dermis and epidermis, and also internal or subsurface wounds such as enhancing closure of incisions following a surgical procedure.

By "treating epithelial wounds" it is meant promoting, accelerating and/or enhancing wound closure, wound contraction, maturation and remodeling, fibroplasia and granulation tissue formation, and/or re-epithelialization.

An "opioid antagonist" binds to and antagonizes (prevents or inhibits signaling of) opioid receptors. Opioid antagonists include nalorphine, levallorphan, cyprodime, naltrindole, norbinaltorphimine, buprinophine, naltrexone and naloxone. Preferred opioid antagonists are antagonists that have affinity for, but do not activate, opioid receptors. Examples of preferred opioid antagonists include naltrexone and naloxone.

For purposes of the present invention, both naltrexone and naloxone, as well as pharmaceutically acceptable salts thereof (e.g., naltrexone hydrochloride, and naloxone hydrochloride) and prodrugs thereof, are suitable for use in the treatment of epithelial wounds.

The IUPAC name for naltrexone is 17-(cyclopropylmethyl)-4,5α-epoxy-3,14-dihydroxymorphinan-6-one. Naltrexone can be described as a substituted oxymorphone, where the tertiary amine methyl-substituent is replaced with methylcyclopropane. Naloxone is also known as dihydroxymorphinan-6-one.

By "prodrug" of a naltrexone and naloxone, it is meant a pharmacological compound administered in an inactive or less active form as compared to naltrexone and naloxone; and is converted in vivo into naltrexone or naloxone after administration. In some embodiments, the prodrug is converted into naltrexone or naloxone in not more than three enzymatic steps. In specific embodiments, the prodrug is converted into naltrexone or naloxone in one or two enzymatic steps. Examples of prodrugs of naltrexone include straight-chain naltrexone-3-alkyl ester prodrugs of 2-7 carbons in chain length described in Stinchcomb et al., *J. Pharmaceutical Sciences* 91: 2571-2578, 2002), as well as the ester, carbonate and carbamate prodrugs described in Valiveti et al., *Pharmaceutical Res.* 22: 981-989 (2005). The entire contents of these references are incorporated herein by reference.

The therapeutic method of treating epithelial wounds involves administration of an effective amount of naltrexone and/or another general opioid antagonist to the epithelial area of a subject for which treatment is desired. For example, treating skin wounds involves topical administration of an effective amount of naltrexone and/or another general opioid antagonist to the wounded area of the skin of a subject.

Topical administration includes directly applying, laying, or spreading on or around the wounded area, e.g., by use of an applicator such as a wipe, a dissolvable film, a dropper, a spray, or through the use of a wound dressing such as a patch.

The opioid antagonist can be combined with a pharmaceutically acceptable carrier and formulated for convenient topical administration. As used herein, a pharmaceutically acceptable carrier includes solvents, dispersion media, isotonic agents and the like. Except insofar as any conventional media, agent, diluent or carrier is detrimental to the recipient or to the solubility or therapeutic effectiveness of the opioid antagonist, its use is appropriate. The carrier can be liquid, semi-solid, e.g. pastes, jelly or cream, or solid carriers. Examples of carriers include water, saline solutions, alcohol, sugar, gel, lipids, liposomes, resins, porous matrices, binders, fillers, coatings, preservatives and the like, or combinations thereof. The opioid antagonist can be combined with the carrier in any convenient and practical manner, e.g., by admixture, solution, suspension, emulsification, encapsulation, absorption and the like, and can be made in formulations such as tablets, capsules, powder, syrup, suspensions, emulsions, ointments, gel, jelly, cream, dressing, patches and the like, that are suitable for topical administration.

In a specific embodiment, the opioid antagonist such as naltrexone or naloxone is formulated as a solution or suspension and is applied topically in the form of liquid drops. Any solution suitable for topical application in which an opioid antagonist (such as naltrexone or naloxone) is soluble can be used; e.g., sterile water, Sorenson's phosphate buffer, among others.

In another specific embodiment, the opioid antagonist is provided in an aqueous-based cream excipient, which can be applied to the wound skin area as a gel, cream or ointment. According to this embodiment, the opioid antagonist can be solubilized first in a liquid carrier (such as water or Sorenson's phosphate buffer), then admixed with a skin cream or gel product.

In other specific embodiments, an opioid antagonist is combined with and incorporated into a solid carrier in the form of patch or dressing, suitable for topical application to skin. In some embodiments, the formulation or skin product is made to have properties such as sustained-release or improved stability. For example, a polymeric matrix composition containing naltrexone can be topically applied to the skin to achieve sustained release.

Compositions containing an opioid antagonist can include additional ingredients, additives or carrier suitable for use in contact on or around the epithelial wounds without undue toxicity, incompatibility, instability, irritation, allergic response, and the like. Additives such as solvents, bases, solution adjuvants, suspending agents, thickening agents, emulsifying agents, stabilizing agents, buffering agents, isotonicity adjusting agents, soothing agents, preservatives, corrigents, flavoring agents, coloring agents, excipients, binding agents, lubricants, surfactants, absorption-promoting agents, dispersing agents, preservatives, solubilizing agents, and the like, can be added to a formulation where appropriate.

The opioid antagonist-containing formulations or compositions of this disclosure can include other active ingredients or active agents for treating epithelial wounds, including, but not limiting to, anti-infective agents, antibiotics, antiviral agents, anti-inflammatory drugs, anti-allergic agents including anti-histamines, vasoconstrictors, vasodilators, local anesthetics, analgesics, intraocular pressure-lowering agents, immunoregulators, anti-oxidants, vitamins and minerals, proteases and peptidases that breakdown endogenous opioids, and the like. In a specific embodiment, an opioid antagonist-containing formulation also includes insulin for topical administration to wounded skin of a diabetic subject.

An opioid antagonist-containing composition of the present invention is administered to a subject in need thereof at an effective amount to treat the wounded epithelial tissue of the subject. The effective amount of the composition for a particular individual can depend on the size and depth of the wound, the type of formulation being applied, the frequency of administration, and the duration of the treatment. It has been found in accordance with the present invention that an opioid antagonist such as naltrexone, dissolved at relatively low concentrations in liquid (e.g., at least $10^{-6}$M, at least $10^{-5}$M, or at least $10^{-4}$ M to $5\times10^{-4}$ M, or any concentration falling in a range between these values, when applied through several different carriers (liquid or semi-solid) to the wounded epithelial area, significantly promotes wound healing. For dermal/epidermal wounds, daily applications, preferably one to three daily applications, are preferred. The final concentration of the opioid antagonist in the formulation applied to a wounded area, whether liquid or semi-solid, is at least 0.003% (w/w), and up to 5-10% (w/w), and generally in the range of 0.1% to 5% (w/w).

The present invention is further illustrated by, but not limited to, the following examples.

EXAMPLES

Materials and Methods
Animals and Induction of Diabetes

Male Sprague-Dawley rats (~150 g) were purchased from Charles River Laboratories (Wilmington, Mass.), and housed under standard laboratory conditions; water and food were available ad libitum. All investigations conformed to the guidelines of The Pennsylvania State University College of Medicine Institutional Animal Care and Use Committee.

Type 1 diabetes (T1D) was induced by intraperitoneal (i.p.) injections of 40 mg/kg streptozotocin (STZ, Sigma, St. Louis, Mo.), on two consecutive days (Klocek et al., *Journal of Ocular Pharmacology and Therapeutics*, 23:89-102 (2007); Havel et al., *Diabetes*, 49:244-252 (2000)). This regimen produced insulin-dependent diabetes in 100% of the animals within 72-96 h; rats with blood glucose levels measuring >350 mg/dl were considered diabetic (DB). Blood glucose levels were monitored from the tail vein using a True Track® Smart System glucometer (Home Diagnostics, Ft. Lauderdale, Fla.) before receiving STZ, and at 1, 4, and 8 weeks following induction of hyperglycemia. Control animals receiving an injection of an equivalent volume of sterile saline were termed "normal". All rats were weighed weekly.

Materials and Methods—Experiment I. Naltrexone and Unwounded Skin
Naltrexone Application Normal (n=24) and diabetic (DB) rats (n=24) were randomized 8 weeks after injections of STZ or saline, and received NTX (Sigma-Aldrich, Indianapolis, Ind.) systemically (30 mg/kg, i.p. or subcutaneous (s.c.) at 0800 h) or topically 3 times daily at 0700, 1200, and 1700 h. For topical applications, NTX was dissolved in Sorenson's phosphate buffer (SPB), KY jelly (KYJ) (K-Y, Personal Products Company, McNeil-PPC, Inc., Skillman, N.J.), Neutrogena moisturizing cream (MCN) (Neutrogena Corporation, Los Angeles, Calif.), or DMSO (VWR, Philadelphia, Pa.). NTX was dissolved in sterile water at dosages of $10^{-4}$M, $10^{-5}$ M or $10^{-6}$ M, and thoroughly mixed into each of the carriers (1:1, v/v); 0.5 ml of saline mixed into corresponding carriers served as the respective vehicle control.

On the day preceding NTX or vehicle treatment, an 8×8 cm area was shaved on the dorsal surface of each rat and 4 circles (approximately 20 mm in diameter) were made with a permanent marker to denote locations of subsequent topical applications and/or skin collection. Using an applicator stick, one ml of carrier containing NTX or vehicle was placed within the demarked areas. Applications of NTX formulations were randomized to different positions. Each animal received NTX in 3 different concentrations, as well as the vehicle, in the same carrier; some rats received only saline in a carrier or were untreated.

DNA Synthesis

To assess cells undergoing DNA synthesis, rats were injected i.p. with 100 mg/kg BrdU (Sigma-Aldrich) 3 and 6 h before euthanasia with Euthasol (Virbac, Fort Worth, Tex.). Appropriate regions of the skin were removed, fixed in 10% buffered formalin, and paraffin sections (6 μm) were stained with anti-BrdU-POD (Invitrogen, Carlsbad, Calif.). BrdU stained cells in the basal layer of the epithelium were counted in four 0.1 mm grids at 250× magnification using 2 sections/specimen; 3 tissue specimens were analyzed for each dosage of NTX in each carrier.

Materials and Methods—Experiment II. Naltrexone and Wound Healing

Full-Thickness Cutaneous Wounds

In a second set of experiments, Normal (n=70) and DB (n=70) Sprague-Dawley rats, 12-14 weeks of age and 8 weeks after injection of STZ, were subjected to wounding. Eight rats/treatment regimen were evaluated over the course of 3 independent experiments. The dorsum of the rat was shaved, and areas (20 mm in diameter) outlined with a marker in order to consistently position the wounds. Animals were anesthetized by i.p. injection of ketamine (60 mg/kg), xylazine (10 mg/kg), and acepromazine (1 mg/kg), and a 6 mm full-thickness circular excisional skin wound was made in the center of the demarked area to the level of the panniculus muscle using an Acupunch (Acuderm Inc., Fort Lauderdale, Fla.). Three wounds per rat were standardized such that the first wound was made 5 cm posterior to the occipital notch at the posterior of the animal's cranium and 1 cm off the midline. The second wound was created 7 cm posterior to the occipital notch at the posterior of the animal's cranium and 1 cm off the midline on the opposite side from the first wound. The third wound was placed 9 cm posterior to the occipital notch at the base of the animal's cranium and 1 cm off the midline on the same side as the first wound. To minimize the effects of diurnal rhythm, surgery was performed between 0800-0900 h. All wounds were left uncovered.

Topical administration of ~0.1 ml of the carrier containing NTX or vehicle, using the dosage and carriers selected from the first experiment, was initiated immediately after wounding (0800 h for those rats receiving agents only once per day, and at 0800, 1200, and 1600 h for those animals receiving 3 applications daily); control rats received the carrier with vehicle either once or three times daily. Some animals in the Normal and DB groups were wounded but untreated.

Photography

Wound size was monitored by capturing images with a digital camera mounted on a tripod set 20 cm from the surface; a ruler was photographed with each wound. Animals were manually restrained without anesthesia for photography. Photographs were taken immediately after surgery and on days 3, 5, 7, 9, and 11. The area of each wound was analyzed using Image ProPlus 6.2 (Media Cybernetics, Inc., Bethesda, Md.). The percent residual wound was calculated at each time point for every rat. At 8 days, wound closure also was quantified according to Pietramaggiori and colleagues (Pietramaggiori et al., *J Surg Res* 160:169-177 (2010)) by measuring contraction, re-epithelialization, and open wound as a percentage of the original wound area. The sum of contracted, re-epithelialized, and open wound area was defined as equaling 100% of the original wound size (Vannas I., *Tissue and Organ Regeneration in Adults*. New York: Springer, 2001).

DNA Synthesis and Histopathology

Cell proliferation was evaluated with BrdU on days 5 and 10 post-wounding as described above. The number of labeled and unlabeled cells in the basal layer of the epithelium was counted in four 0.1 mm grids at 250× magnification, and sampled from regions adjacent, and 0.5 mm peripheral, to the edge of the wound site. Three Normal and 3 DB rats receiving MCN+vehicle or MCN+NTX 3 times daily were injected with BrdU.

On day 20 following creation of the wound, some rats were euthanized and the original wound areas as well as tissue peripheral to the wound that encompassed the 20 mm diameter circle were excised and fixed in 10% neutral buffered formalin. Tissues were processed for paraffin embedding; sections were stained with hematoxylin and eosin. The thickness of the epithelium covering the granulation tissue was measured with an ocular micrometer. Five measures/section from 7-8 wounds/treatment group were evaluated at 250× magnification.

Data Analysis

Body weights and glucose measurements were analyzed with Student's two-tailed t-test. Areal measurements of defects (e.g., percent residual wound, contraction), thickness of the epithelium, and DNA labeling indexes were evaluated using analysis of variance (ANOVA) with subsequent planned comparisons made utilizing Newman-Keuls tests.

Results

Experiment I. Naltrexone and Unwounded Skin

Figure 1:
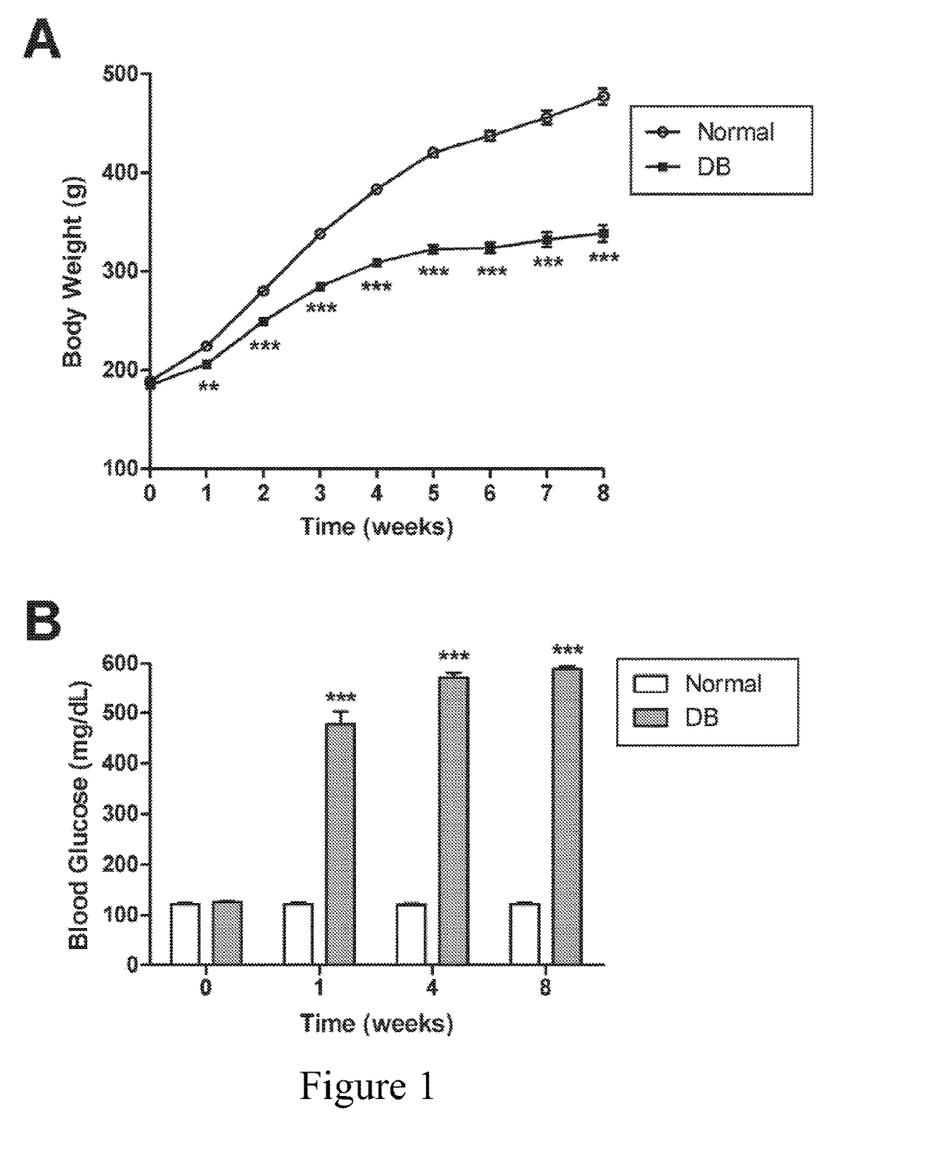
FIG. 1. Body weights (A) and glucose levels (B) of rats rendered diabetic with STZ (DB) or those untreated receiving saline (Normal). A: Body weights were recorded prior to STZ injection (week 0), and weekly thereafter. B: Blood glucose levels were recorded before (week 0) and at 1, 4, and 8 weeks after STZ administration. Values represent means±SEM for at least 5 animals/group at each time point. Significantly different from Normal at $P<0.01$ and *$P<0.001$.

All rats were hyperglycemic within 72 h of STZ injection, with blood glucose levels for Normal and DB animals being 119±4 and 569±9 mg/dL, respectively (FIG. 1). The body weights of DB rats were reduced by 8% to 28% from Normal cohorts beginning 1 week after STZ injection and continuing throughout the experimental period (FIG. 1). Rats in the DB group were not provided with insulin. No animals died from hyperglycemia.

Relative to the BrdU labeling index of 8.1±0.3% in basal cells of the cutaneous epithelium of Normal rats, systemic injections of 30 mg/kg NTX by the i.p. or s.c. routes elevated BrdU labeling by 172% and 51%, respectively. With respect to a labeling index of 8.1±0.5% in the skin of animals with DB, i.p. and s.c. injections of NTX increased BrdU incorporation by 181% and 59%, respectively.

Figure 2:
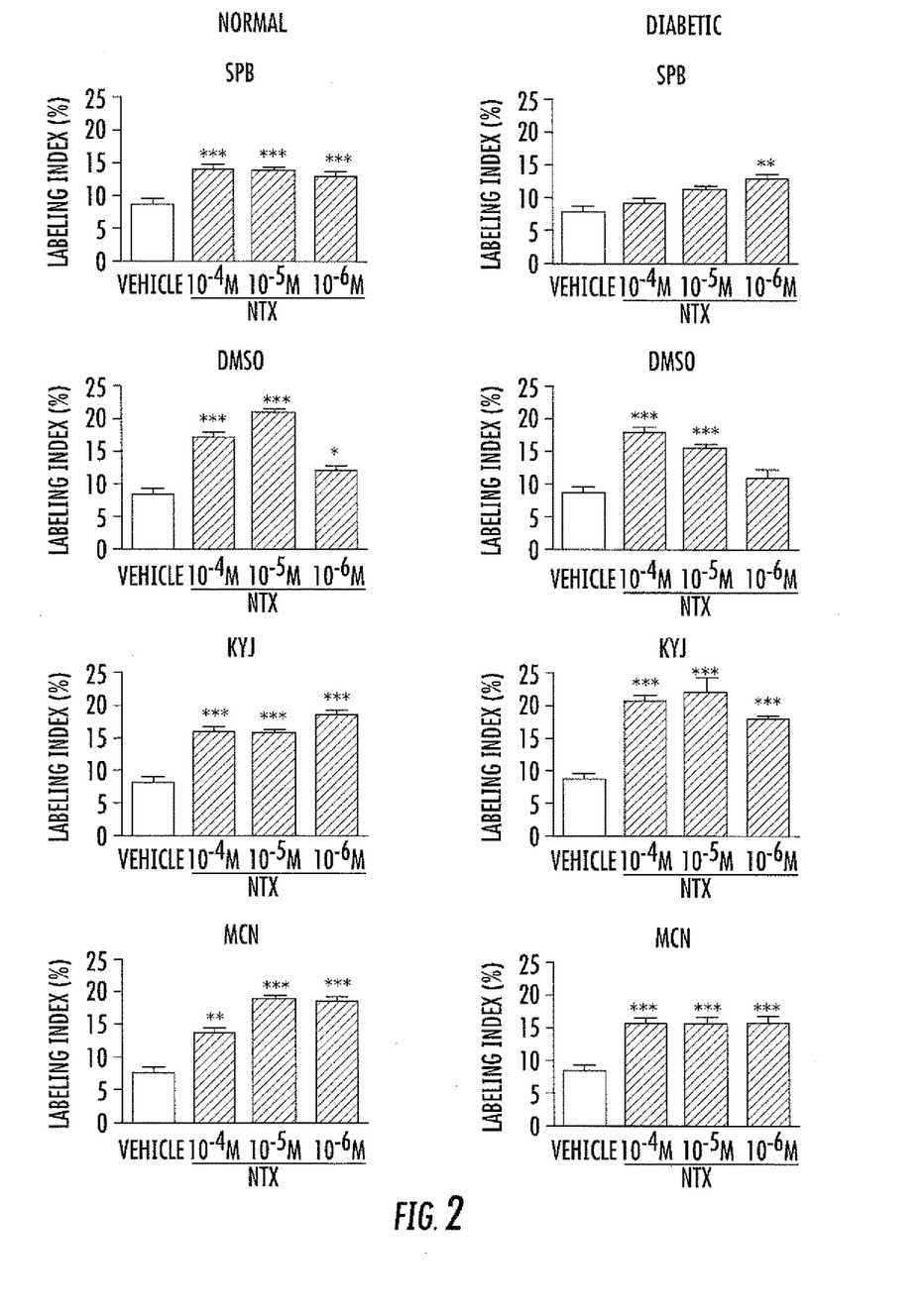
FIG. 2. Histograms of the labeling indexes in stratum basale on the dorsum of rats topically treated with NTX ($10^{-4}$ M, $10^{-5}$ M, or $10^{-6}$ M) dissolved in Sorenson's phosphate buffer (SPB), DMSO, KY Jelly (KYJ), or Neutrogena moisturizing cream (MCN); control rats received the corresponding vehicle (Vehicle). Animals received 3 topical applications of NTX. At 3 and 6 hr before euthanasia, animals received injections of BrdU (100 mg/kg; i.p.). Two-way ANOVA for Treatment (4 carriers and 4 concentrations/carrier) and Condition (diabetic, Normal) was performed. There was no overall effect for Condition; Treatment was significant at $P<0.001$, F=5.59 (15, 288). Data represent means±SEM. Based on one-way ANOVA for each carrier and Condition, significantly different from respective values for vehicle-treated rats at *$P<0.05$, $P<0.01$, and *$P<0.001$.

The effects of topical application of NTX ($10^{-4}$ M to $10^{-6}$M) dissolved in four different carriers that had different properties (e.g., absorption, density) were examined in Normal and DB rats (FIG. 2). Topical NTX dissolved in any of the 4 carriers consistently elevated (43-132%) DNA synthesis from baseline levels in Normal animals. Animals receiving NTX in SPB displayed the lowest level of increase in BrdU incorporation in the skin (43-56%) compared to baseline values, whereas rats treated with different dosages of NTX in MCN exhibited some of the greatest changes from baseline (73-132%). In the DB rats, topical exposure to NTX at all 3 dosages markedly elevated labeling indexes from baseline levels when delivered in KYJ (103-147%) or MCN (85-89%). NTX at concentrations of $10^{-4}$ and $10^{-5}$ M delivered in SPB to DB rats had no effect on BrdU incorporation. The opioid antagonist combined with DMSO only was efficacious at concentrations of $10^{-4}$ and $10^{-5}$ M.

To examine whether topical application of NTX had systemic ramifications, some rats were treated with MCN+ NTX ($10^{-5}$ M) or MCN+vehicle at different positions on their dorsum. The skin treated with MCN+NTX had a labeling index of 18.0±0.9% compared to 8.1±0.7% for wounds on the same animal receiving MCN+vehicle; the basal epithelium of separate, untreated rats had a labeling index of 8.2±0.5%.

Figure 3:
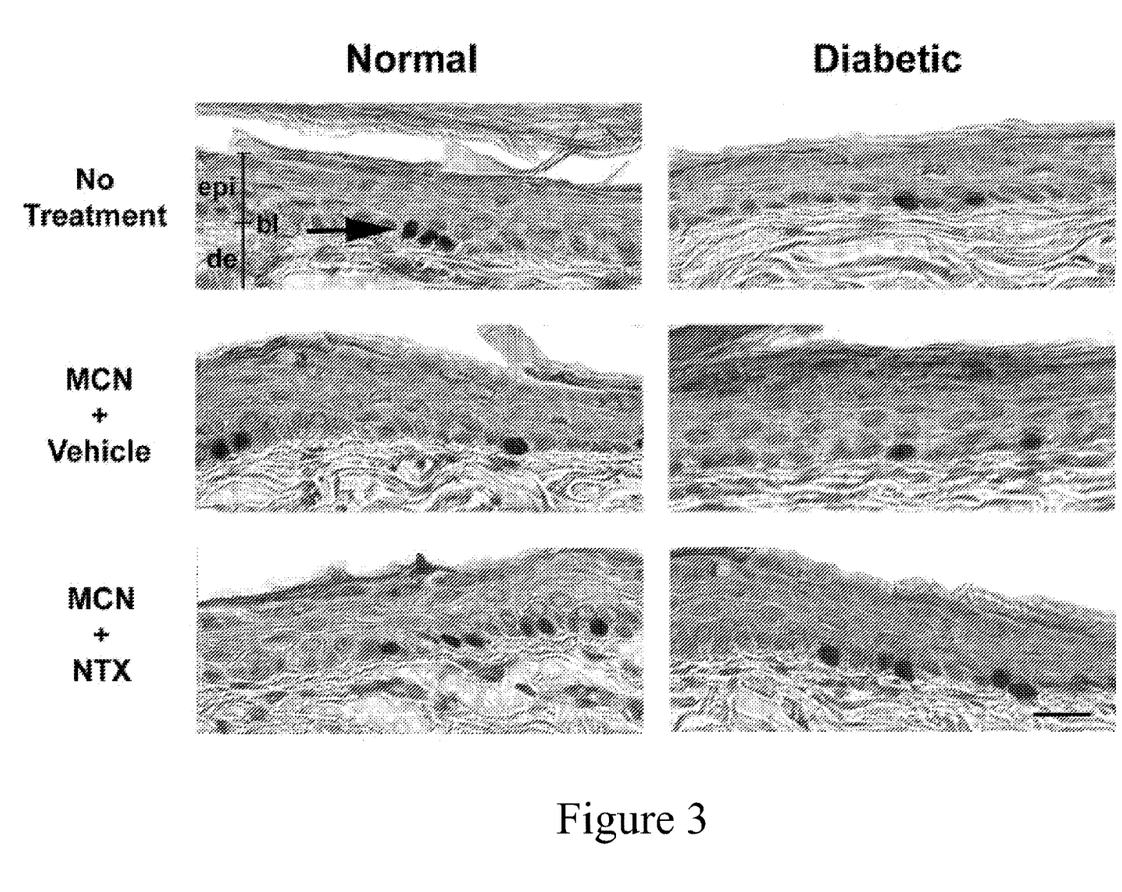
FIG. 3. Histological preparations of dorsal skin from Normal and Diabetic rats subjected to $10^{-5}$ M NTX in Neutrogena moisturizing cream (MCN+NTX), moisturizing cream only (MCN+Vehicle), or no treatment. Sections were stained with anti-BrdU antibodies and counterstained with hematoxylin. Note increases in BrdU-positive cells (arrow) in the NTX-treated groups. bl, basal layer; epi, epidermis; de, dermis. Bar=12 μm.

Examination of the skin, both grossly and by histological measures, revealed a similar appearance in Normal and DB rats receiving vehicle or any dosage of NTX in any carrier. The morphology of the treated skin was comparable to that in animals not exposed to any agent (FIG. 3).

Experiment II. Naltrexone and Full-Thickness Wounds

Based on the labeling index data from the first experiment, NTX at $10^{-5}$ M applied in two topical delivery systems, KYJ and MCN, was chosen for subsequent experiments examining the effects of opioid antagonist blockade on full-thickness wound healing. Normal and DB rats expressed body weight and glucose patterns similar to those in FIG. 1. All rats tolerated the wounding procedure without problems (e.g., normal food consumption).

Normal and Diabetic Wound Healing

Using a 6 mm trephine, the calculated wound size was 28.3 mm$^2$, and wounds that deviated more than 10% were not included for analysis. Evaluation of wound closure in Normal and DB rats revealed that the area of residual wound in DB animals was 24%, 44%, and 132% greater on days 5, 7, and 9 following surgery relative to those of Normal rats (FIG. 5A).

Number of Applications of NTX and Efficacy of Wound Healing

Figure 4:
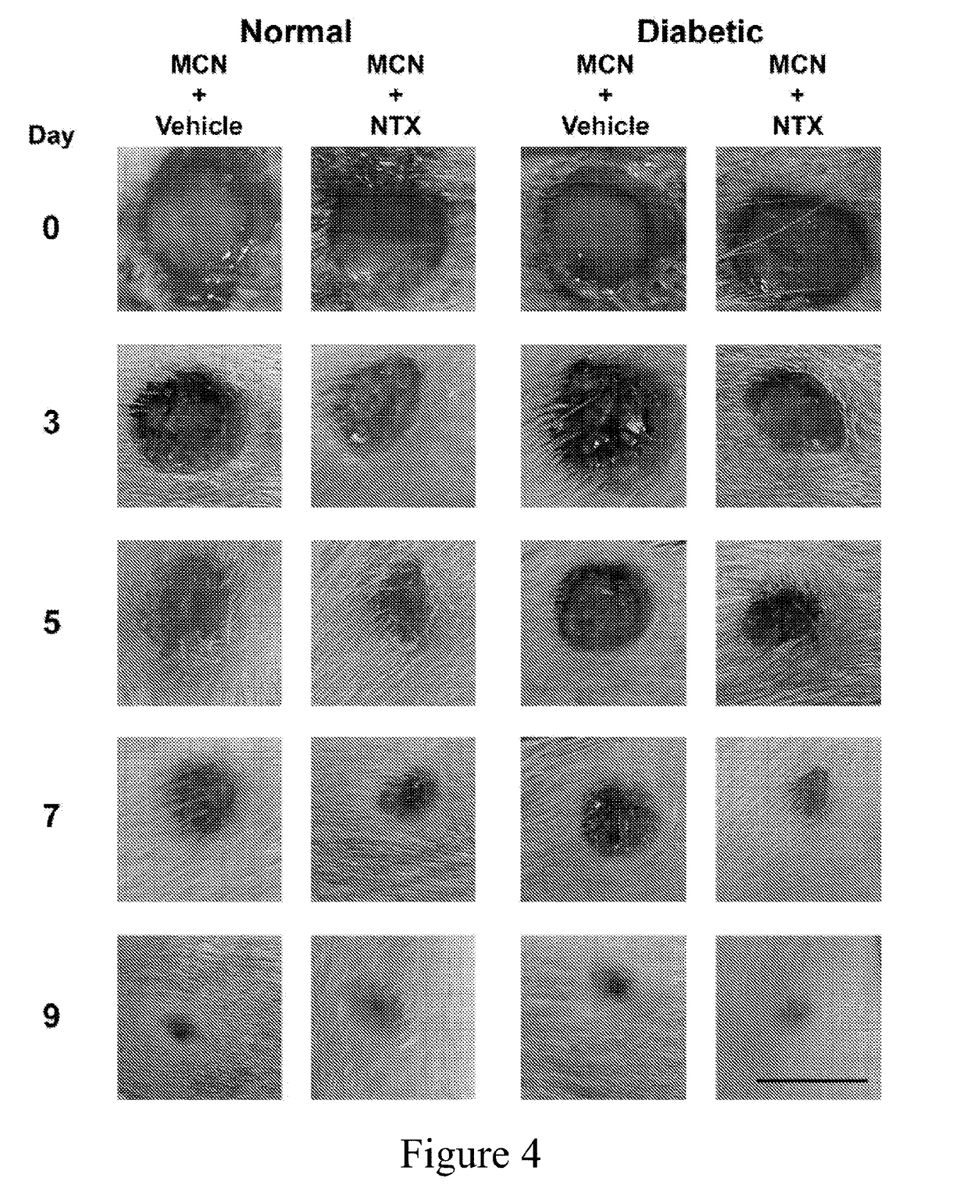
FIG. 4. Photomicrographs of full-thickness wounds created on the dorsal surface of Normal and Diabetic rats. Wounds were treated 3 times daily with either $10^{-5}$ M NTX dissolved in Neutrogena moisturizing cream (MCN+NTX) or moisturizing cream alone (MCN+Vehicle) and photographed on day 0, 3, 5, 7, and 9 following wounding. Bar=6 mm.
Figure 5:
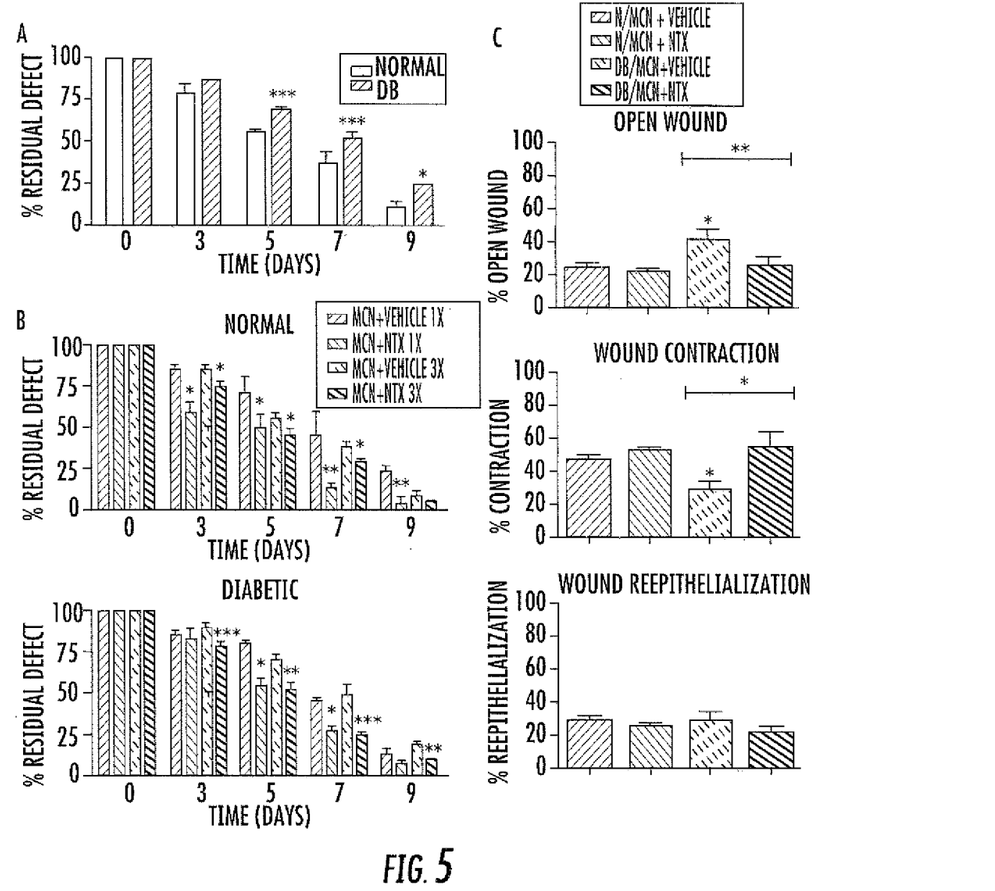

To examine the effects of topical application of NTX on the healing of full-thickness wounds in Normal and DB rats, an investigation was initiated to study whether the number of daily applications of NTX was critical (FIGS. 4, 5). Within 3 days of a single or three times daily regimen of $10^{-5}$ M NTX in MCN to Normal rats, wound areas were reduced 30% and 11%, respectively, relative to that of animals receiving MCN+vehicle (FIG. 5B). Wound sizes on days 3, 5, 7, and 9 in NTX-treated Normal animals were smaller than in cohorts receiving MCN+vehicle, with reductions ranging from 31-82% and 11-23% for the one and three times daily regimens, respectively; all data were statistically significant except for the value for the three times daily group on day 9. DB animals subjected to once daily application of MCN+NTX also had a decrease in wound size compared to DB rats exposed to vehicle, but with only 32% and 42% reductions recorded on days 5 and 7, respectively. However, in regard to the DB animals, MCN+NTX given three times daily consistently accelerated wound closure, with this group displaying mean residual wounds that were reduced 13% to 57% from DB rats treated with MCN+ vehicle.

In addition to absolute wound closure, wound contraction and re-epithelialization, two of the main mechanisms contributing to healing (Pietramaggiori et al., *Journal of Surgical Research*, 160:169-177 (2010); Yannas, *Tissue and Organ Regeneration in Adults*, New York: Springer (2001)) were analyzed on day 8 in the MCN group (FIG. 5C). DB rats receiving MCN+vehicle had an open wound 82% larger than that of Normal animals treated with MCN+vehicle, and rates of wound contraction were reduced by 38%; re-epithelialization, however, was comparable between these two groups. DB rats subjected to MCN+NTX were similar in all parameters (i.e., wound size and contraction, re-epithelialization) to that of Normal animals given MCN+ vehicle, with the size of the open wound and wound contraction of DB animals treated with MCN+NTX being one-half that of DB animals treated with MCN+vehicle.

Figure 6:
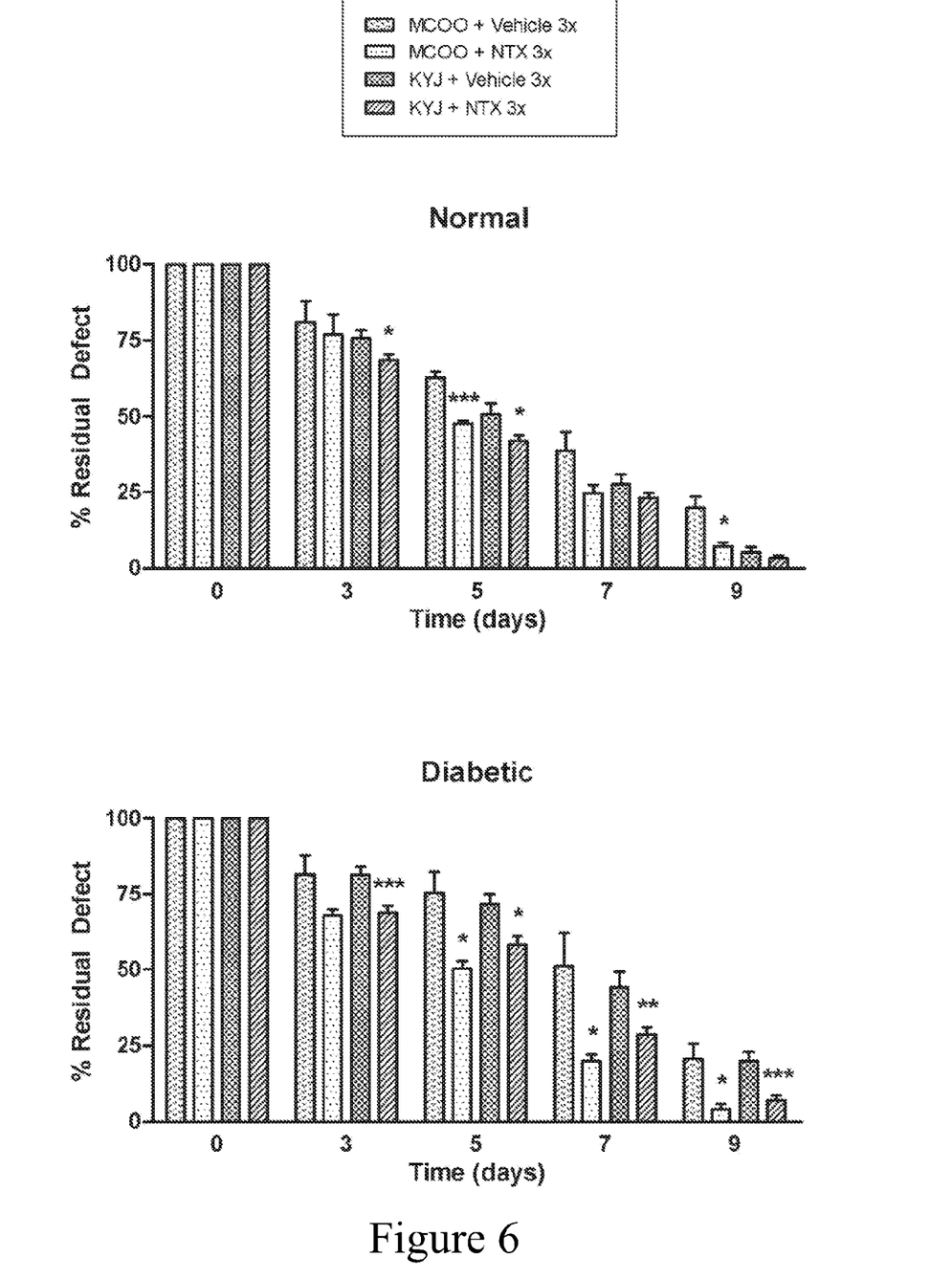

To examine whether the effects of NTX on wound closure were dependent on a particular type of moisturizing cream (i.e., Neutrogena), some animals were treated with NTX in Oil of Olay (MCOO) (Procter & Gamble, Cincinnati, Ohio). In comparison to Normal animals exposed three times daily to MCOO+vehicle, those rats receiving $10^{-5}$ M NTX in MCOO had 24 to 65% smaller residual wounds on days 5, 7, and 9 (FIG. 6). DB animals subjected three times daily to MCOO+NTX had wounds that were 33-80% smaller than counterparts receiving MCOO+vehicle on days 5, 7, and 9.

To address the question whether the action of NTX was reliant only on moisturizing creams, Normal and DB rats were treated three times daily with NTX in KYJ (FIG. 6). Wounds in Normal animals receiving KYJ+NTX were 10-17% smaller on days 3 and 5 relative to wounds treated with KYJ+vehicle. In contrast to DB rats receiving vehicle in KYJ, DB animals subjected three times daily to KYJ+ NTX had wounds that were 15-65% smaller on days 3, 5, 7, and 9.

Histopathology

Figure 7:
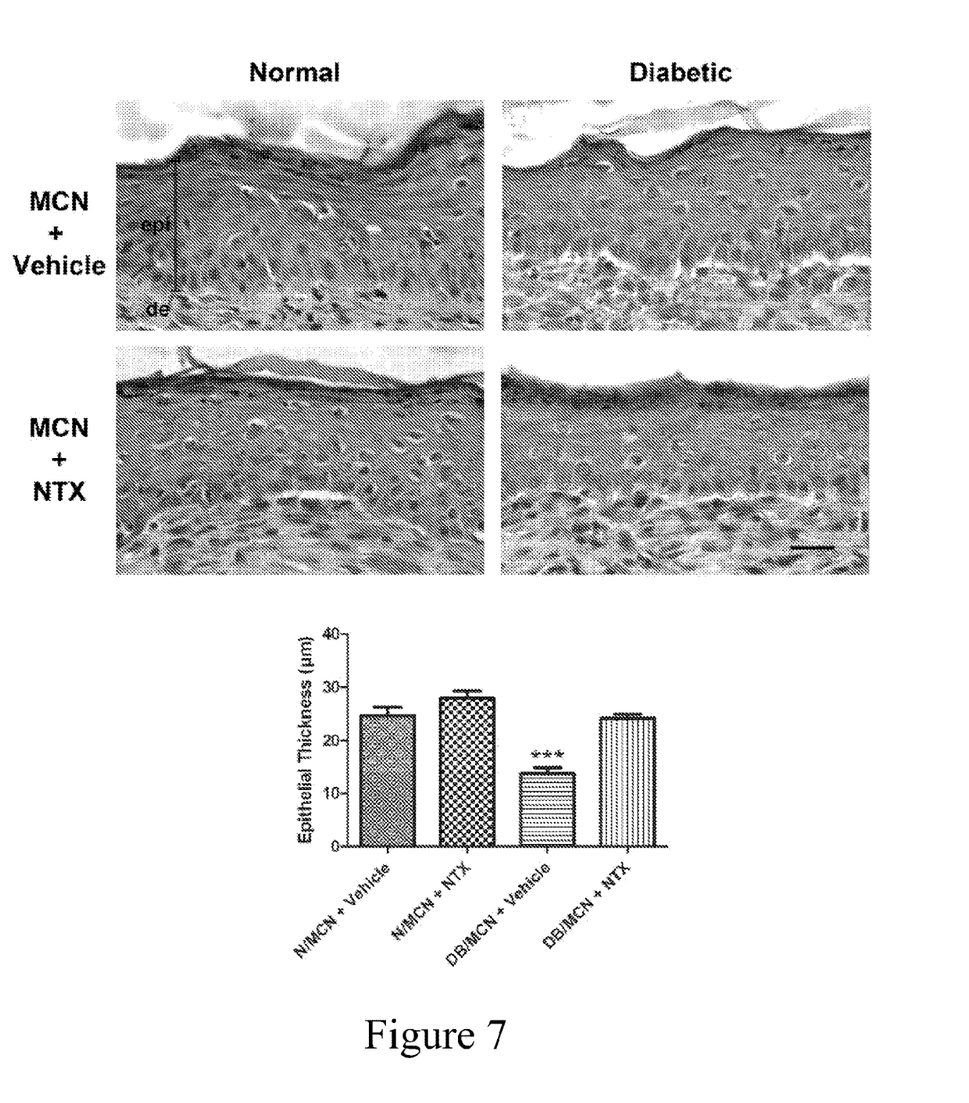
FIG. 7. Photomicrographs of skin from Normal and Diabetic rats collected 20 days after the creation of 6 mm full-thickness wounds. Some wounds were treated 3 times daily with $10^{-5}$ M NTX dissolved in Neutrogena moisturizing cream (MCN+NTX) or receiving vehicle alone (MCN+Vehicle). Sections were stained with hematoxylin and eosin. epi, epidermis; de, dermis. Bar=12 μm. Histograms of epithelial thickness (μm) measured 20 days after wounding. Values represent means±SEM. Significantly different from N/MCN+Vehicle at ***$P<0.001$.

The overall pathology of the wounded days following surgery was evaluated with hematoxylin/eosin stains (FIG. 7). The general structure of the epithelium between Normal and DB rats receiving vehicle or NTX appeared to be similar (e.g., absence of necrotic cells). However, in comparison to a width of the epithelium overlying the granulation tissue of 24.6±1.6 μm in Normal rats, DB rats receiving vehicle had a 44% reduction. Normal animals treated with NTX, as well as DB rats subjected to NTX, did not differ in the thickness of the epithelium relative to Normal animals receiving vehicle.

DNA Synthesis

Figure 8:
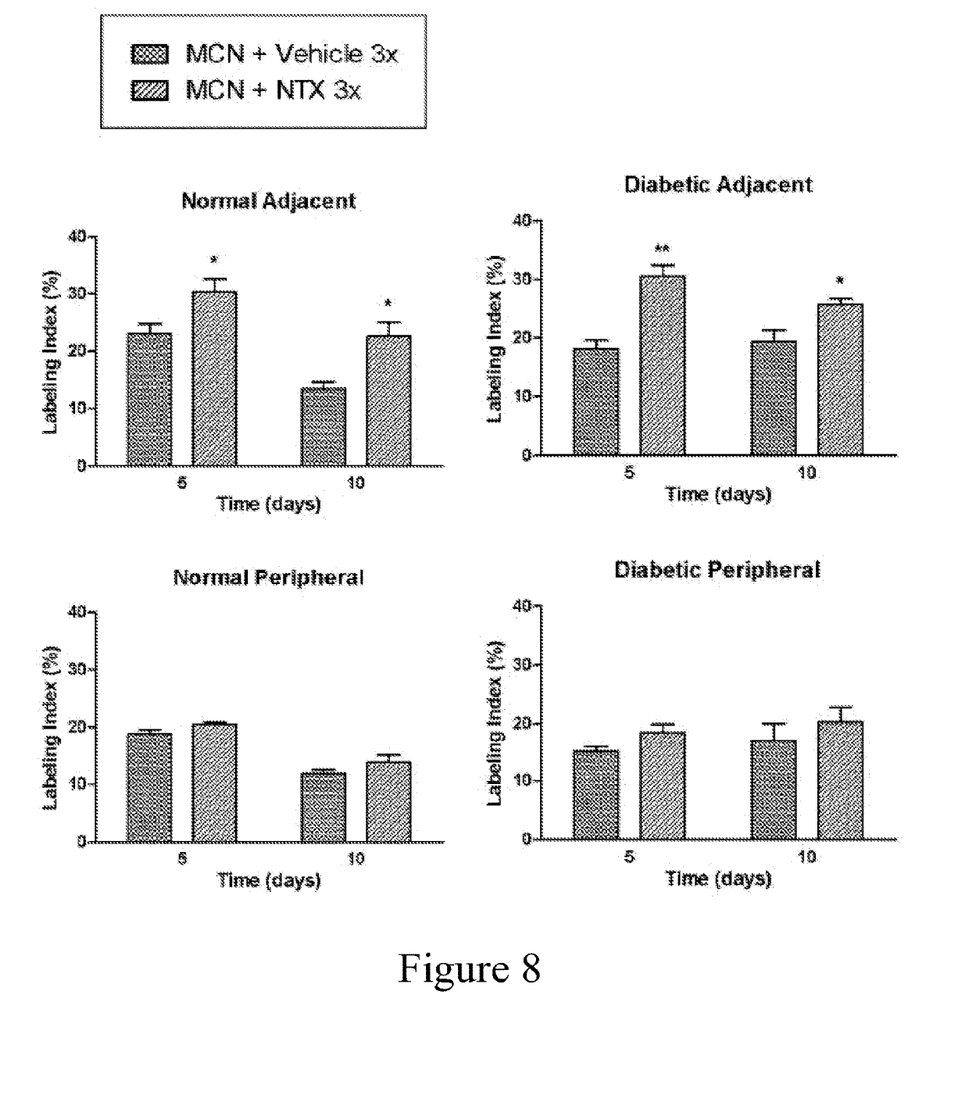
FIG. 8. Histograms of the labeling indexes of basal epithelial cells in skin adjacent to and peripheral to wounds in Normal and Diabetic rats after topical treatment 3 times daily with $10^{-5}$ M NTX dissolved in Neutrogena moisturizing cream (MCN+NTX 3×) or receiving vehicle alone (MCN+Vehicle 3×); data were collected after 5 or 10 days of treatment. Values represent means±SEM. Significantly different from their respective vehicle at * $P<0.05$ and **$P<0.01$.

In order to begin to decipher the mechanism of NTX action with respect to wound healing in DB mice, and keeping in mind previous reports that NTX targets cell proliferation (Zagon et al., *Journal of Invest Dermatology*, 106:490-497 (1996); Zagon et al., *Diabetes*, 51:3055-3062 (2002); Zagon et al., *Journal of Vascular Surgery*. 37:636-643 (2003); Blebea et al., *Journal of Vascular Surgery*, 32:364-373 (2000); Zagon et al., *Immunobiology*, 216:173-183 (2011); Zagon et al., *Immunobiology*, 216:579-590 (2011); Wilson et al., *Cell Prolif*, 33:63-73 (2000)), Normal and DB rats subjected 3 times daily to vehicle or $10^{-5}$ M NTX in MCN were assessed for BrdU labeling on days 5 and 10 following wounding (FIG. 8); skin adjacent and peripheral to the site of injury was evaluated. MCN+NTX altered DNA synthesis in the basal epithelium of skin adjacent to the wounds, but not in the peripheral region in both DB and Normal rats. In the DB rats, those treated with MCN+NTX had a 72% and 36% increase in labeling index on days 5 and 10, respectively, in skin adjacent to the wound. In Normal animals there was an increase of 30% and 69% on days 5 and 10, respectively, in labeled cells located in skin adjacent to the wound of Normal rats compared to cohorts receiving vehicle.

Experiment III.

To study the effects of opioid antagonists on wound healing in a Type 2 diabetic and general obesity model, wound healing was compared between wild type and Lepr$^{db}$ (also referred to as db/db) mutant mice. Mice homozygous for the diabetes spontaneous mutation (Lepr$^{db}$) become identifiably obese around 3 to 4 weeks of age. Plasma insulin levels become elevated beginning at 10 to 14 days and blood sugar levels become elevated beginning at four to eight weeks. These mice show delayed wound healing compared to wild type mice.

Figure 9:
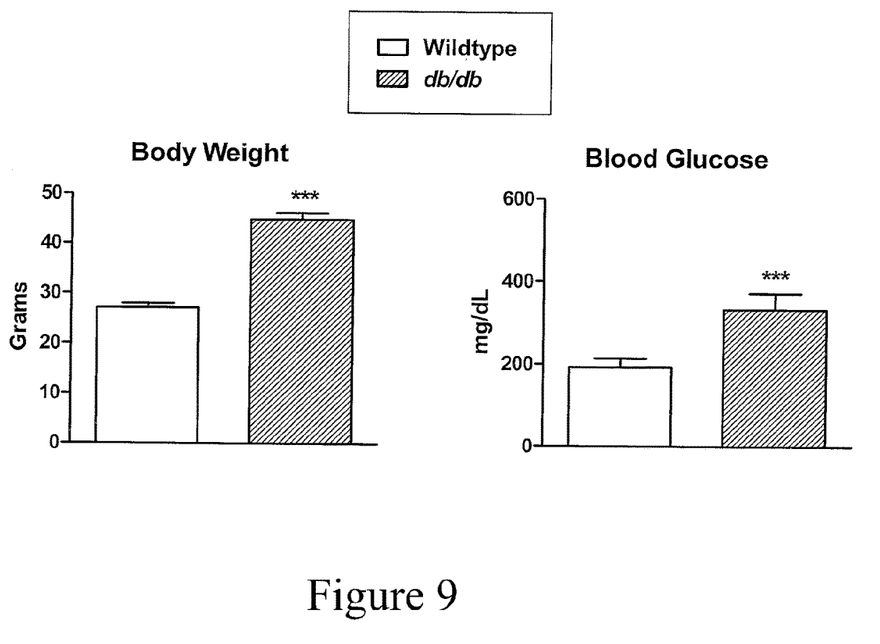
FIG. 9. Body weights and blood glucose levels of 8-week old Type 2 diabetic (db/db) mice and wildtype C57Bl/6 mice. Mice were purchased from Jackson Laboratories and housed under standard laboratory care. Tail vein blood was obtained and glucose levels were measured by a TrueTrak glucometer. Values represent means±SEM; n=6-10 mice/treatment group. Data were analyzed using t-tests; significantly different from wildtype at $p<0.001$ (***).

Mice were purchased from Jackson Laboratories and housed under standard laboratory care. Body weights and blood glucose levels of 8-week old Type 2 diabetic (db/db) mice and wild type C57B1/6 mice were obtained (FIG. 9). Tail vein blood was obtained and glucose levels were measured by a TrueTrak glucometer. Values represent means±SEM; n=6-10 mice/treatment group. Data were analyzed using t-tests; significantly different from wild type at p<0.001 (*). As seen in FIG. 9**, eight week-old db/db mice have significantly higher body weight and blood glucose levels than wild type C57B1/6 mice.

Figure 10:
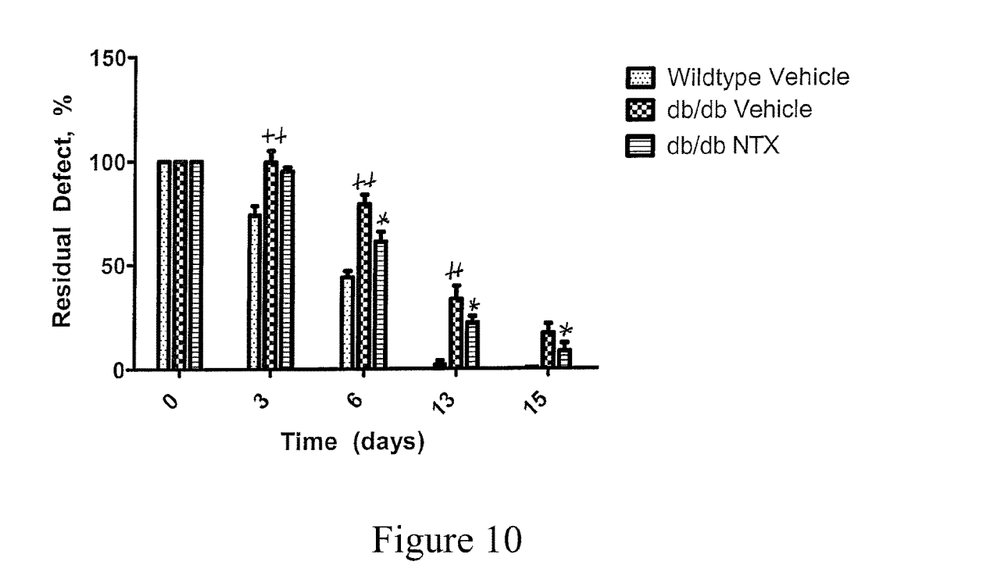
FIG. 10. Residual defect (%) on days 3, 6, 13, and 15 following formation of a 5-mm circular full-thickness cutaneous wound created on the dorsum of Type 2 diabetic (db/db) and wildtype mice. Db/db mice were treated with either $10^{-5}$ M Naltrexone (NTX) in moisturing cream (vehicle), or vehicle alone; wildtype mice received vehicle only. Applications were made 3 times daily for 15 days. Values represent means±SEM for at least 5 wounds/treatment group at each time point. Significantly different from wildtype vehicle values at $p<0.01$ (++). Significantly different from db/db vehicle values at $p<0.05$ (*).

To study wound healing, a 5-mm circular full-thickness cutaneous wound was created on the dorsum of db/db and wild type mice. Db/db mice were treated with either 10$^{-5}$ M Naltrexone (NTX) in moisturing cream (vehicle), or vehicle alone; wild type mice received vehicle only. Applications were made 3 times daily for 15 days. As seen in FIG. 10, db/db mice show a significantly higher percent residual defect on days 3, 6, and 13 following wound formation, relative to wild type. However, db/db mice treated with NTX show significant improvement in would healing relative to db/db mice treated with vehicle only by days 6, 13, and 15. Significantly different from wildtype vehicle values at p<0.01 (++). Significantly different from db/db vehicle values at p<0.05 (*).

These studies show that topical NTX treatment improves wound healing in Type 2 diabetes in addition to Type 1 diabetes. In addition, as db/db mice are also a model for obesity in general, this study show that topical opioid antagonists are beneficial not only for treating wounds in the diabetic population, but for treatment of wounds in a normal population as well.

Discussion

With the use of a well-characterized model of T1D wherein rats developed typical physiological characteristics observed in diabetic humans such as hyperglycemia, weight loss, and poor wound healing (Zagon et al., *Diabetes*, 51:3055-3062 (2002); Klocek et al., *Journal of Ocular Pharmacology and Therapeutics*, 23:89-102 (2007); Havel et al., *Diabetes*, 49:244-252 (2000)), a major finding in this study is that disruption of endogenous opioid-opioid receptor interfacing with the opioid antagonist NTX can increase DNA synthesis in basal epithelial cells of the skin in T1D animals, as well as normal (non-diabetic) cohorts. The effects of NTX on cell proliferation were not toxic, relatively short-acting, and not dependent on either concentration (within a 100-fold range applied topically) or route of administration (systemic or topical). NTX administered by topical delivery was localized in influencing DNA synthesis, as cells subjacent to the carrier with drug were elevated in BrdU labeling but not basal epithelial cells distant from NTX application.

Since NTX is a pure opioid antagonist and devoid of direct biological action (Blumberg et al., *Agonist and Antagonist Actions of Narcotic Analgesic Drugs*, 110-119 (1973); Sawynok et al., *Life Science*, 25:1621-1632 (1979)), the upregulation of DNA synthesis by interruption of opioid peptide-opioid receptor interfacing indicates that one or more endogenous opioid systems present in human and animal cutaneous epithelium (Zagon et al. *Journal of Invest Dermatology*, 106:490-497 (1996)) are intact and function as tonically active repressors of DNA synthesis under pathophysiological conditions related to T1D. Although some studies report that epithelium (e.g., ocular surface) of T1D animals has a subnormal level of DNA synthesis (Zagon et al., *Diabetes*, 51:3055-3062 (2002)), it is interesting to note that the basal layer of epithelial cells in the skin of diabetic animals had a rate of DNA synthesis comparable to that of normal rats, suggesting that at least 2 months after the induction of diabetes, abnormalities in cell replicative events were not evident in the skin.

Based on these initial experiments, the inventors characterized the effects of this agent on repair of full-thickness cutaneous wounds in T1D and T2D animals. Evaluation of closure rates showed that the wounds of diabetic animals were significantly slower to heal than those in normal animals, and that topical NTX placed in these carriers restored the rate of wound closure to levels comparable to and often exceeding that of normal animals. Animals with diabetes had markedly reduced wound contraction compared to normal cohorts, but T1D and T2D animals receiving topical NTX were comparable to normal subjects. The structural appearance of the closed wounds in the diabetic animals receiving NTX was similar to that of normal animals, indicating that the increased rate of wound repair was not accompanied by abnormal morphological events. Although once daily application of NTX was sufficient to increase the rate of cutaneous wound closure in DB rats, three daily applications were superior.

The successful use of NTX for topical delivery demonstrated herein raises the question of whether this drug has systemic repercussions. NTX is a small hydrophilic molecule that has been suggested to not have physicochemical properties necessary to achieve therapeutic doses for transdermal delivery (Wermeling et al., *Proc Natl Acad Sci USA*, 105:2058-2063 (2008); Stinchcomb et al., *Journal of Pharm Science*, 91:2571-2578 (2002)), but is known to enter human and animal cells rapidly by passive diffusion (Cheng et al., *American Journal of Physiology*, 297:R844-R852 (2009)). The studies presented herein reveal that NTX had a localized but not systemic action, with DNA synthesis altered only at the site of delivery. Moreover, the inventors employed a very small concentration of NTX that is non-toxic, but highly efficacious in terms of wound repair. Thus, in considering the application of topical NTX for the treatment of wounds clinically, these studies show that this is feasible in terms of biocompatability, and lack of toxicity and systemic action. Additionally, problems in compliance should be minimized by the localized effects of this opioid antagonist.

The present finding that an opioid antagonist can restore the delayed rate of cutaneous wound healing recorded in diabetes to that of normal animals has some parallels with previous reports concerning corneal re-epithelialization in T1D rats (Zagon et al., *Diabetes*, 51:3055-3062 (2002); Klocek et al., *Journal of Ocular Pharmacology and Therapeutics*, 23:89-102 (2007)). These include: i) efficacy of both topical and systemic NTX routes of delivery, ii) response to similar concentrations (e.g., 10$^{-5}$M) of NTX, iii) NTX-induced increases in the rate of wound closure for both diabetic and normal animals, iv) necessity for multiple daily applications of NTX to achieve optimal healing rates, and v) DNA synthesis as a principle target for NTX action. However, some differences between the skin and cornea of diabetic and normal animals as to NTX's effects on wound healing should be noted. First, corneal wound healing is confined to the ocular surface epithelium and is reliant on re-epithelialization. In contrast, full-thickness cutaneous wound repair is related to both the epithelium and the stroma, and contraction plays a major role in repair. Second, the carrier for NTX in the cornea included an antibiotic, while no antibiotics were employed in the present study, although inclusion of an antibiotic and/or other additional component is contemplated for the invention described herein. Both studies show that heightened opioid peptide—opioid receptor interaction as it relates to DNA synthesis and wound healing occurs in T1D, and blockade of this interfacing is demonstrated to reverse the delayed repair of cutaneous, as well as corneal, wounds in a hyperglycemic environment.

The present results demonstrate that opioid receptor blockade can reverse delayed wound healing, such as is present in diabetes, to normal levels, indicating that endogenous opioid systems contribute to delayed wound healing. The glucose levels of the diabetic rats in this study were not only extraordinarily high compared with those of humans, but the duration of hyperglycemia was sustained for 3 months, emphasizing the magnitude of the diabetic condition. The data suggest that even in the face of such uncontrolled diabetes, wound healing could be restored with topical NTX. This finding provides evidence that the action of NTX must be extremely potent, and that opioid-receptor interactions are capable of being disrupted by NTX in animals with persistently high glucose levels.

Impaired wound healing is a major complication in both T1D and T2D (Guo et al., *Journal Dent Res,* 89:219-229 (2010); Boulton et al., *Lancet,* 366:1719-1724 (2005); O'Loughlin et al., *International Journal of Lower Extremity Wounds,* 9:90-102 (2010); Usui et al., *Journal of Histochem Cytochem,* 56:687-696 (2008)). The studies herein represent a paradigm shift regarding the etiology and pathogenesis of complications from diabetes by identifying opioid peptides and opioid receptors as key players in this disease. It is important to recognize that NTX is an FDA-approved drug used at far higher dosages in the treatment of addiction (e.g., drug abuse, tobacco, gambling) (Kirchmayer et al. *Addiction,* 97:1241-1249 (2002); Swift, *American Journal of Health Syst Pharm,* 64:S12-S22 (2007)). In addition, an ongoing Phase I clinical trial is assessing the safety of topical NTX in the eye for the treatment of diabetic keratopathy, and the results heretofore indicate that NTX is without toxicity. The utilization of small dosages of NTX in a topical application with localized but not systemic effects eliminates any potential adverse events, even for patients using opioids for pain management.

What is claimed is:

1. A composition for treating an epidermal or dermal wound in a diabetic subject, the composition comprising an effective amount of an opioid antagonist and a pharmaceutically acceptable carrier.

2. The composition of claim 1, wherein said opioid antagonist is naltrexone, naloxone, or a prodrug or salt thereof.

3. The composition of claim 1, wherein said composition is formulated as a solution.

4. The composition of claim 2, wherein said opioid antagonist is present in said composition at a concentration of at least $10^{-6}$ M.

5. The composition of claim 1, wherein said composition is formulated as a cream or gel.

6. The composition of claim 1, wherein said composition is in the form of a patch or dressing.

7. The composition of claim 1 further comprising at least one additional active ingredient for treating epithelial wounds.

8. The composition of claim 1, wherein the epidermal or dermal wounds comprise full-thickness wounds.

9. The composition of claim 1, wherein the opioid antagonist promotes healing of the dermal or epidermal wounds through interaction with the opioid growth factor receptor.

* * * * *